United States Patent [19]

Feldman

[11] Patent Number: 5,248,258
[45] Date of Patent: Sep. 28, 1993

[54] DENTAL IMAGING MATRIX BAND AND METHOD FOR MAKING OR SETTING CROWNS AND BRIDGES ON PREPARED TEETH

[76] Inventor: Richard L. Feldman, 11 Wintergreen Dr., Easton, Conn. 06612

[21] Appl. No.: 893,061

[22] Filed: Jun. 3, 1992

[51] Int. Cl.⁵ ............................ A61C 5/04; A61C 5/10
[52] U.S. Cl. ..................................... 433/39; 433/223
[58] Field of Search ................... 433/39, 40, 155, 213, 433/223

[56] References Cited

U.S. PATENT DOCUMENTS

| | | | |
|---|---|---|---|
| 4,575,805 | 3/1986 | Moermann et al. | 433/223 |
| 4,837,732 | 6/1989 | Brandestini et al. | 433/223 |
| 5,092,022 | 3/1992 | Duret | 433/213 |

Primary Examiner—Cary E. O'Connor
Attorney, Agent, or Firm—Arthur T. Fattibene; Paul A. Fattibene

[57] ABSTRACT

This disclosure is directed to a dental imaging matrix band and a method for making a dental prosthetic restoration such as a ¾ crown, full crown, or fixed bridge with the use of a CAD-CAM machine. This is attained by encircling a tooth or teeth prepared for receiving a ¾ crown, full crown or fixed bridge restoration by a matrix band having an enlarged beaded peripheral edge or lip which can be optically read by a scanner of a CAD-CAM machine. The optical image of the tooth or teeth and the encircling matrix band is transformed by the CAD-CAM machine into a signal which controls the operation of the forming or milling portion of the CAD-CAM machine to shape a block of dental material into the shape of a ¾ crown, full crown or fixed bridge to be fitted to the prepared tooth or teeth in accordance with the optical image of the prepared tooth or teeth. The matrix band is defined by a strip of thin non-reflective metallic material having a longitudinal edge thereof defining an enlarged bead which can be optically scanned by a CAD-CAM machine; the image of which being transformed into a signal enabling the CAD-CAM to machine a ¾ crown, full crown or fixed bridge to be received by the prepared tooth or teeth.

12 Claims, 1 Drawing Sheet

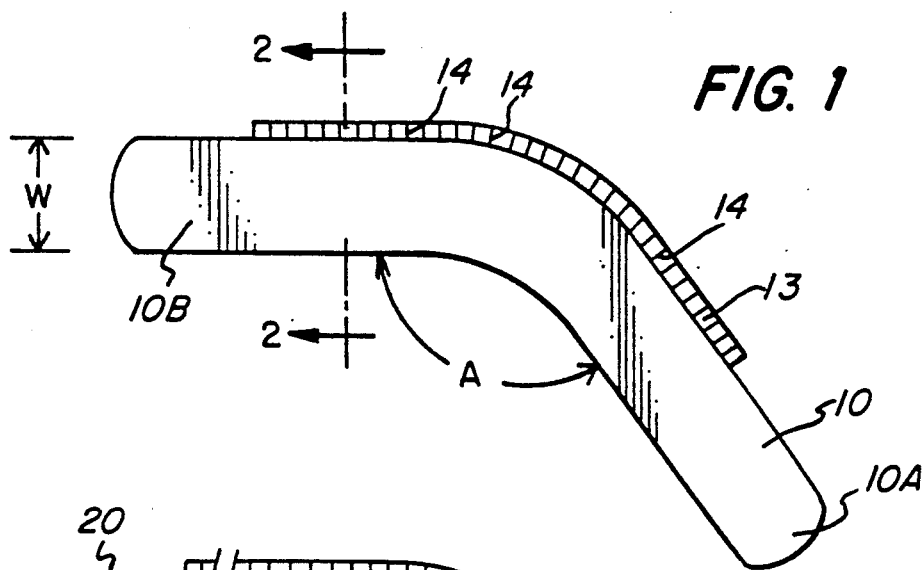
FIG. 1
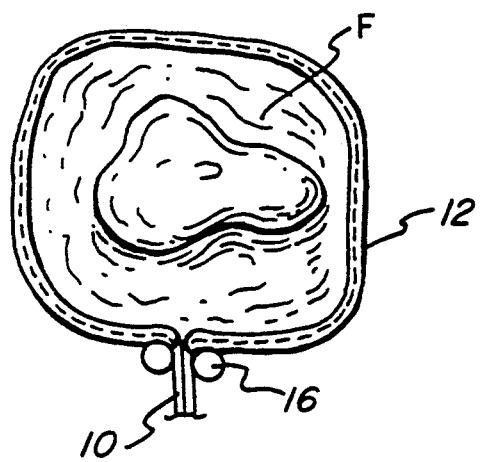
FIG. 3
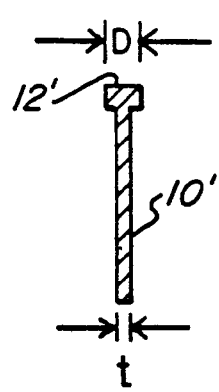
FIG. 6
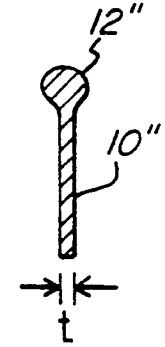
FIG. 5
FIG. 4
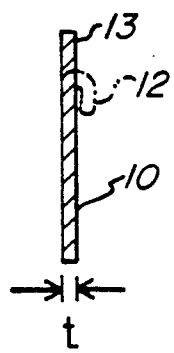
FIG. 2

DENTAL IMAGING MATRIX BAND AND METHOD FOR MAKING OR SETTING CROWNS AND BRIDGES ON PREPARED TEETH

FIELD OF INVENTION

This invention is directed to a dental imaging matrix band and method for facilitating the making of crowns and bridges in conjunction with a CAD-CAM machine such as a SIEMENS CEREC.

PRIOR ART

Prior to this invention, dentists have utilized a CAD-CAM machine for making various types of restorative inlays, onlays and porcelain laminates for teeth. A CAD-CAM machine is a device which records an optical image of a tooth which has been prepared for an inlay, onlay or porcelain laminate, and which image is thereafter transformed into a signal transmitted to a forming wheel to machine or mill a block of ceramic material into the shape of the inlay, onlay or porcelain laminate to be placed in or on the prepared tooth in accordance with the optical image perceived by the CAD-CAM machine. The benefit of utilizing the CAD-CAM technique for making inlays, onlays or porcelain laminates is to eliminate the tedious and time consuming task of taking a traditional impression of the prepared tooth and thereafter sending the impression to a laboratory for making the final inlay, onlay or porcelain laminate. Not only is the laboratory work tedious and time consuming, it has the further disadvantage that such tooth restorations could not generally be completed in a single visit, thereby requiring the dentist to provide the patient with a temporary restoration and requiring the patient to return for another visit or treatment after the lab work has been completed.

A noted deficiency of the known CAD-CAM machines is that they are incapable of being used to make a ¾ crown, a full crown restoration or a fixed bridge. This is because the prepared tooth for a ¾ crown, a full crown or a fixed bridge cannot be imaged by the CAD-CAM machines whereby a proper signal can be transmitted to the forming wheel to machine or mill the ceramic block for making the required crown or bridge.

SUMMARY OF THE INVENTION

According to the present invention, the foregoing noted deficiency of the CAD-CAM type machines for making dental restorations is obviated by a specifically constructed matrix band which is adapted to be fitted to the prepared tooth for receiving the full or partial crown restoration or fixed bridge. The matrix band is constructed so as to enable the CAD-CAM machine to simulate an optical image of the outer periphery of the prepared tooth or area in a manner such that a proper signal can be transmitted to the milling portion of the machine to mill a full or partial crown or fixed bridge in accordance with the shape of the optical image defined by the matrix band. The matrix band is formed as a narrow blank of sheet material, e.g. a thin gauge flexible metallic strip which is non-reflective. Along the upper encircling portion of the band, there is provided a beaded edge to define or simulate the optical peripheral portion of the tooth or area to receive the full or partial crown or fixed bridge. The beaded edge can be formed by forming the beaded portion as an integral part of the band. The beaded edge may also be formed by providing a marginal flap or extension which can be readily reversely folded to define an optical visual edge adapted to be read by the optical scanner of the CAD-CAM machine. The opposed edges of the band are retained by a conventional band holder.

IN THE DRAWINGS

FIG. 1 is a side view of a matrix band embodying the invention adapted to form a full or partial crown.

FIG. 2 is a sectional view taken along line 2—2 of FIG. 1 wherein the dotted line shown illustrates the reversely folded position of the marginal flange to define the beaded edge.

FIG. 3 is a plan or top view of the matrix band of FIG. 2 disposed in encircling position about a prepared tooth.

FIG. 4 illustrates a sectional view of a modified embodiment.

FIG. 5 is a sectional view of another modified embodiment.

FIG. 6 is a side view of a matrix band embodying the invention for making a fixed bridge restoration.

DETAIL DESCRIPTION

This invention is directed to a method and device for making a prosthetic tooth restoration in the form of crowns, partial crowns or fixed bridges with the use of a CAD-CAM machine.

Referring to the drawings, FIG. 1 illustrates a side view of a metallic blank 10 from which the matrix band embodying the invention is formed. As shown, the blank 10 comprises a flat elongated blank or strip having angularly disposed sections 10A and 10B. The included angle A between sections 10A and 10B preferably falls in a range of 120 degrees to 140 degrees with a 130 degree angle being considered the optimal angle for making, e.g. a full or partial ¾ crown. For a bridge matrix band as shown in FIG. 6, the length of the band is made longer than that required for the crown matrix band of FIG. 1, as the bridge matrix band is required to encircle three or more teeth. The fixed bridge matrix band 20 as illustrated in FIG. 6 is provided with portions 20A and 20B which are longer than that of the crown matrix band 10 of FIG. 1 so that the band 20 may encircle three or more teeth. Also, the angle A is in the range of 160 degrees to 180 degrees with a preferred angle of 170 degrees. In all other respects, the construction is similar to that herein described. There must be an angle A, as shown in FIGS. 1 and 6, to allow the gingival edge of the band to tightly contact the tooth, diverging occlusally. This allows the optical impression to clearly see the floor F or "bottom line" of the tooth. The width "w" of the matrix blank is approximately 6 millimeters for a premolar tooth and 10 mm for a molar tooth, or generally equal to the height of the tooth to be restored, which extends above the gum line.

According to this invention, the encircling portion of the band or blank 10, adapted to circumscribe the tooth or teeth which have been prepared to receive either a ¾ crown, a full crown or fixed bridge, is provided with an upper beaded edge 12. In the form of the invention shown in FIGS. 1 and 2, the beaded edge 12 of the matrix band 10 is defined by a marginal flap or extension 13 which is adapted to be reversely folded to define the beaded edge 12 as best seen in FIG. 2 in the dotted line showing. To facilitate the reverse folding of the marginal flap 13, a series of radial slits 14 may be longitudinally spaced along the marginal flap 13. The upper edge or beaded edge 12 of the band is shaped to define or approximate the upper peripheral contour of the tooth to be restored to form the basis of the signal transmitted to the milling portion of the CAD-CAM machine. Preferably, the width of the flap 13 which extends beyond the edge of the blank 10 is approximately 2 millimeters. By reversely folding the flap 13 to overlie the thickness of the band 10, the thickness of the beaded edge so formed of the band encircling the prepared tooth is doubled. This thickened edge of the band enables the optical scanner to accurately see the simulated periphery of the tooth which is translated into a signal that indicates the height or Z axis of the ¾ crown, full crown or fixed bridge to be milled by the CAD-CAM machine.

The thickness "t" of the blank 10, as illustrated in FIG. 2, is approximately 0.03 to 0.04 millimeters. By the reverse fold of the marginal flap 13, the thickness of the upper or beaded edge 12 is doubled.

FIG. 4 illustrates a further embodiment of the invention. In this form of the invention, the upper beaded edge 12' of the band 10' is formed as an integrally formed cross-head portion wherein the cross section of the blank 10' is "T" shaped. In all other respects, the band 10' is similar to that hereinbefore described.

FIG. 5 illustrates another modified embodiment. In this form of the invention, the beaded portion 12" of matrix band 10" is defined as rounded or circular beaded portion. If desired, the beaded edge 12' or 12" may comprise a separate member which is tack welded or otherwise secured or connected to the band or strip 10 or 10'.

In use, the matrix band 10, 10' or 10" of FIGS. 2, 4 or 5 respectively, is disposed about the tooth which has been prepared for receiving the partial or full crown as shown in FIG. 3, wherein the beaded edge 12, 12', 12" defines the upper periphery of the tooth to be restored. It will be understood that the free ends of the band are held together by a conventional matrix band holder 16, e.g a Tofflemine holder. With the matrix band 10, 10', 10" in place as shown in FIG. 4, the optical scanner of the CAD-CAM machine is placed over the tooth to transmit the optical image to the screen of the CAD-CAM. The angle A of the matrix band provides an intimate, tight fit to the tooth gingivally diverging away from the bottom or floor of the prepared tooth, allowing a clear optical impression of the floor of the tooth. The thickened beaded occlusal edge of the band simulates the walls of a tooth, creating an optical illusion or false cavosurface margin. Through the internal working of the CAD-CAM, the optical image perceived is transformed into a series of digital signals which allows the milling portion of the machine to mill an accurate ¾ crown, full crown or fixed bridge which is approximately shaped for application to the prepared tooth or teeth and to fit inside the simulated cavosurface margins created by the matrix band. The improved matrix band of this invention thus permits a dentist to utilize the CAD-CAM for making ¾ crowns, full crowns or fixed bridges simply and quickly, whereby the ¾ crown, full crown or fixed bridge is made and installed in a single sitting and without resorting to the heretofore tedious and time consuming traditional laboratory work. Thus, the dentist can now prepare a tooth for receiving a ¾ crown, a full crown or bridge, make the computer generated restoration, install and finish the same all in a single sitting.

To insure forming an accurate optical image, it is preferred that the material of the band be non-reflective. This can be attained by roughing the surface of the band to reduce shine or reflection.

After the ¾ crown, full crown or fixed bridge has been milled to fit the shape of the prepared tooth and inside the simulated cavosurface margin created by the matrix band in accordance with the optical image made possible by the matrix band, the crown is polished and finished to harmonize with the patient's natural teeth.

While the invention has been described with respect to the illustrated embodiments, it will be readily understood and appreciated by those skilled in the art that variations and modifications may be made without departing from the spirit or scope of the invention.

What is claimed is:

1. A dental imaging matrix band comprising
   an elongated blank of relatively thin flexible sheet material having a width substantially equal to the height of a tooth extending beyond the gum line,
   said blank being sufficiently long and flexible for encircling at least one prepared tooth,
   means forming a bead having a thickness greater than that of said blank extending along an edge portion thereof for defining the upper periphery edge of a tooth when said blank is disposed about a tooth.

2. A dental imaging matrix band as defined in claim 1 wherein said blank includes angularly disposed sections to define an included angle ranging between 120 and 180 degrees.

3. A dental imaging matrix band as defined in claim 2 wherein said blank is formed of a non-reflective metal strip.

4. A dental imaging matrix band as defined in claim 2 wherein said means comprises a marginal flap extending beyond the width of said blank and formed integral therewith, said flap being adapted to be reversely folded along an edge portion of said blank.

5. A dental imaging matrix band as defined in claim 4 and including a plurality of longitudinally spaced radial slits formed along said flap to facilitate the reverse folding of said flap.

6. A dental imaging matrix band as defined in claim 2 wherein said means comprises an integrally formed cross-head to impart a "T" shape cross-section to said blank.

7. A dental imaging matrix band as defined in claim 2, wherein said means comprises an integrally formed rounded beaded shape cross-section to said blank.

8. A dental imaging matrix band as defined in claim 2 wherein said blank has a width of approximately 6 millimeters and a thickness in the range of 0.03 to 0.04 millimeters for a premolar ¾ crown or premolar full crown.

9. A dental imaging matrix band as defined in claim 2 wherein said blank has a width of 10 millimeters and a thickness in the range of 0.03–0.04 millimeters for a molar ¾ crown or full crown.

10. A dental imaging matrix band as defined in claim 2 and having a length adapted to encircle at least three prepared teeth to determine the area for a fixed bridge.

11. A method of making and setting a crown on a tooth to be restored comprising the steps of:
    preparing a tooth to receive a crown,
    circumscribing the prepared tooth with a matrix band having an optical readable floor and periphery,
    taking an optical image of the prepared tooth with circumscribing matrix band with an optical scanner of a CAD-CAM machine, whereby said CAD- CAM machine converts said optical image into a digital signal, milling the crown material in accordance to said digital signal to shape the crown to be placed in the prepared tooth, and finishing said milled crown to said prepared tooth.

12. A method of making and setting a prosthetic tooth restoration comprising:

preparing the area for receiving the prosthetic restoration, circumscribing the prepared area with a matrix band having an optical readable floor and periphery, taking an optical image of the prepared area with the circumscribing matrix band with the optical scanner of a CAD-CAM machine whereby said optical image is converted into a digital signal, milling a block of restoration material in accordance to said digital signal to shape the prosthetic restoration, applying said milled prosthetic restoration to the prepared area, and finishing said milled prosthetic restoration in place in the prepared area.

* * * * *